US009297757B2

(12) United States Patent
Canova et al.

(10) Patent No.: US 9,297,757 B2
(45) Date of Patent: Mar. 29, 2016

(54) LASER GAS ANALYZER

(75) Inventors: Lorenzo Canova, Paris (FR); Mathieu Rougnon, Courbevoie (FR)

(73) Assignees: SAINT-GOBAIN GLASS FRANCE, Courbevoie (FR); SAINT-GOBAIN EMBALLAGE, Courbevoie (FR)

( * ) Notice: Subject to any disclaimer, the term of this patent is extended or adjusted under 35 U.S.C. 154(b) by 117 days.

(21) Appl. No.: 13/984,213

(22) PCT Filed: Feb. 9, 2012

(86) PCT No.: PCT/FR2012/050286
§ 371 (c)(1),
(2), (4) Date: Aug. 7, 2013

(87) PCT Pub. No.: WO2012/168588
PCT Pub. Date: Dec. 13, 2012

(65) Prior Publication Data
US 2013/0313436 A1 Nov. 28, 2013

(30) Foreign Application Priority Data

Feb. 14, 2011 (FR) .................................... 11 51167

(51) Int. Cl.
*G01J 5/02* (2006.01)
*G01N 21/61* (2006.01)
(Continued)

(52) U.S. Cl.
CPC ............... *G01N 21/61* (2013.01); *C03B 5/235* (2013.01); *G01N 21/3504* (2013.01); *G01N 2201/0612* (2013.01)

(58) Field of Classification Search
CPC ... G01N 21/61; G01N 21/39; G01N 21/3504; G01N 2201/0612; C03B 5/235
USPC ............................................. 250/341.1, 343
See application file for complete search history.

(56) References Cited

U.S. PATENT DOCUMENTS 5,984,998 A 11/1999 Ottesen et al.

2004/0047782 A1* 3/2004 Mori et al. ................... 423/210
2006/0038194 A1* 2/2006 Terashima et al. ............. 257/98

FOREIGN PATENT DOCUMENTS

CN 101939265 A 1/2011
EP 2 108 937 10/2009
(Continued)

OTHER PUBLICATIONS

International Search Report Issued May 31, 2012 in PCT/FR12/50286 Filed Feb. 9, 2012.
(Continued)

*Primary Examiner* — David Porta
*Assistant Examiner* — Abra Fein
(74) *Attorney, Agent, or Firm* — Oblon, McClelland, Maier & Neustadt, L.L.P.

(57) ABSTRACT

The invention relates to a device for measuring the concentration of a molecule, such as CO, NO or $NO_2$, in a gaseous atmosphere at a temperature above 1200° C. in a chamber, said molecule having an absorption line at a wavelength between 4 and 8 µm, said device comprising an emitter that emits laser radiation with a wavelength corresponding to that of the absorption line, said emitter emitting the laser radiation through a first window and then through said atmosphere, said window being made of a solid material having, for a material thickness of 1 mm, a transmittance greater than 50% at the wavelength of the laser radiation, the laser radiation being analyzed after having passed through said atmosphere by an analyzer that determines the absorption of the laser radiation by the molecule in the gaseous atmosphere, the window being placed on or in a wall of the chamber, where appropriate via an insert, in order to prevent the hot atmosphere of the chamber escaping therefrom. The invention provides a continuous measurement during normal operation of the installation on which it is mounted. The device according to the invention may equip a glass furnace and continuously measure the concentration of gaseous species in the hot atmosphere during normal operation of the furnace. This allows the burners of the furnace to be adjusted during operation.

21 Claims, 2 Drawing Sheets

Figure 1:
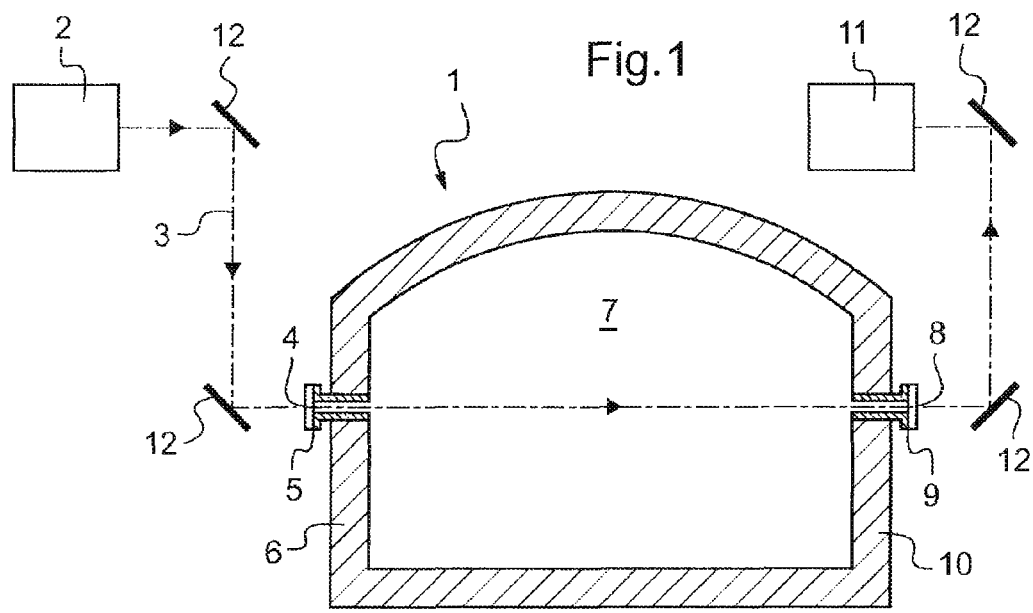

(51) Int. Cl.
*C03B 5/235* (2006.01)
*G01N 21/3504* (2014.01)

(56) References Cited

FOREIGN PATENT DOCUMENTS

| FR | 2 859 283 | | 3/2005 |
|----|-----------|---|--------|
| FR | 2 859 468 | | 3/2005 |
| FR | 2859283 | A1 * | 3/2005 |
| FR | 2859468 | A1 * | 3/2005 |
| JP | 11-295213 | A | 10/1999 |
| JP | 2001-523818 | A | 11/2001 |
| JP | 2005-265609 | A | 9/2005 |
| JP | 2007-170841 | A | 7/2007 |

OTHER PUBLICATIONS

French Search Report Issued Aug. 5, 2011 in FR 1151167 Filed Feb. 14, 2011.
Combined Chinese Office Action and Search Report issued Dec. 15, 2014 in Patent Application No. 201280008773.3 (with English Translation).

* cited by examiner

LASER GAS ANALYZER

CROSS REFERENCE TO RELATED APPLICATIONS

The present application is a 35 U.S.C. §371 national stage patent application of International patent application PCT/FR2012/050286, filed on Feb. 9, 2012, published as WO 2012/168588 on Dec. 13, 2012, the text of which is incorporated by reference, and claims the benefit of the filing date of French application no. 1151167, filed on Feb. 14, 2011, the text of which is also incorporated by reference.

The invention relates to the field of analyzing gas concentrations in hot atmospheres such as those of furnaces, especially glass furnaces.

The concentration of combustion gas (CO, NO, $NO_2$, etc.) produced by each burner of a glass furnace is usually measured by an extractive technique. According to this technique, the air is extracted at a discrete point by a cooled pyrometer via ducts passing through the walls or in the rear of the regenerator chambers. This air is then filtered, dried and analyzed by electrochemical sensors. The gas concentration measurement may then be used for regulating the combustion. Because of the problem of steam cooling and condensing in the pyrometer, the extractive measurement may be carried out only for limited time periods. This prevents a continuous measurement of the combustion gases and therefore prevents effective and continuous control of the combustion in the furnace.

As an alternative solution to this extractive technique for measuring hot gases, the inventors now have the idea of using one or more lasers emitting around an absorption line of the molecule species of interest. To measure in particular NO, $NO_2$, CO or other gaseous species at the typical temperatures of those of glass furnaces (generally above 1200° C.), it is proposed to use one particular type of semiconductor laser, called a quantum cascade laser which emits in the mid-infrared spectral range (3 μm to 24 μm). To carry out the measurement, the beam is sent through the wall of the chamber (especially the wall of a furnace or a flue gas duct) containing the hot atmosphere to be analyzed in order to pass through this atmosphere. The term "chamber" is to be taken in a broad sense, being any container of the atmosphere to be analyzed. For example, this chamber may be a duct sending the combustion flue gas to the outside of a furnace, that is to say for example a duct linking a furnace to a generator and serving alternately as air intake duct to a burner and flue gas collector duct. Once the absorption length, the temperature and the pressure are known, the concentrations of the molecular species of interest are obtained from the transmission measurement for each wavelength (using the Lambert-Beer law). The term "wall" is understood to mean any wall in the broad sense, that is to say any physical boundary of the chamber (including the roof of a furnace), provided that it is possible for the laser beam to pass through the hot atmosphere of the chamber without this beam encountering any obstacle that absorbs it too greatly. Preferably, the laser beam is injected via a window according to the invention and also made to exit via a window according to the invention, the laser encountering between these two windows only the hot atmosphere of the chamber. If the laser passes through a glass furnace, it passes through the gaseous atmosphere above the glass. This atmosphere may contain fine particles.

The laser solution according to the invention allows continuous measurement during the normal operation of the installation on which it is mounted. In particular, the device according to the invention may equip a glass furnace and continuously measure the concentration of gaseous species in the hot atmosphere during normal operation of the furnace. In particular, this furnace may operate continuously. It is not necessary for the laser radiation to be continually present throughout the operation of the system to be monitored (such as for example a furnace). This is because the variations in gas concentrations are sufficiently slow so that measurements spaced apart by one second or a few seconds are amply sufficient for assessing the variations in gas concentrations. Such measurements are carried out by a pulsed laser.

In particular, the device according to the invention may be applied to analyzing the atmosphere of any type of glass furnace, such as melting furnaces with overhead burners or submerged burners, horseshoe-fired furnaces, cross-fired furnaces, the latter possibly being equipped with regenerators or recuperators, and glass-forming furnaces, such as float glass furnaces for forming flat glass.

In general, it is necessary to have two windows placed in the walls of the chamber containing the gas to be analyzed, in order to inject and extract one or more laser beams. Working in the mid-infrared imposes constraints on the design of the windows. In particular, it is necessary for the window to be sufficiently transparent at these wavelengths and to withstand the high temperature of the gaseous atmosphere. A material having a very low thermal expansion such as fused silica does not constitute the ideal material because it is not very transparent at these wavelengths.

U.S. Pat. No. 3,154,821 teaches a device for inspecting the interior of a furnace that includes a window comprising two parallel glass plates the space therebetween being coursed by water. As other documents of the prior art, the following may be mentioned: JP 3274385 (A), JP 8014522 (A), US 2004/156420 and U.S. Pat. No. 7,283,243. U.S. Pat. No. 5,984,998 teaches a device for analyzing the combustion gas in a chamber, using a laser beam, the device being at a certain distance from the chamber and protected by heat protection plates.

The invention proposes an optical system which makes it possible to transmit at least one beam of laser radiation in the mid-infrared through a wall of a chamber containing a hot atmosphere, in particular for measuring the concentration of combustion gas such as, for example, CO, NO or $NO_2$. This continuous metrology system makes it possible to optimize the combustion and thus improve the energy efficiency of the furnace and the reduction of harmful gases. The system comprises a window which is relatively transparent to the measurement spectral range, it being possible for said window to be cooled by a double water/air cooling system in order to withstand for a long time the normal operating conditions of the chamber (such as a furnace), which entails good temperature resistance and good heat shock resistance. The window may in particular be placed on or in a wall of the chamber, where appropriate via an insert. Thus, the window may in particular be incorporated in an insert, said insert being placed on or in a wall of the chamber. By virtue of this type of optical insert, it is possible to emit one or more laser beams into the chamber through the same window or different windows, the orifices in the walls remaining sealed. This sealing of the orifices prevents a (possibly harmful) gas of the hot atmosphere escaping from inside the chamber. The measurement length may be determined exactly, since this corresponds substantially to the distance between the entry window and the exit window. As a result, the gas concentration measurement is precise. The term "sealing" means above all that the gas of the atmosphere inside the chamber is prevented from escaping via the orifice provided with the window. This sealing may be partial or complete, depending on the case.

Thus, the invention relates in the first instance to a device for measuring the concentration of a molecule in a gaseous atmosphere at a temperature above 1200° C., said molecule having an absorption line at a wavelength between 4 and 8 µm, said device comprising an emitter that emits laser radiation with a wavelength corresponding to that of the absorption line, said emitter emitting the laser radiation through a first window and then through said atmosphere, said window being made of a solid material having, for a thickness of 1 mm, a transmittance greater than 50% and preferably greater than 80% at the wavelength of the laser radiation, the laser radiation being analyzed after having passed through said atmosphere by an analyzer that determines the absorption of the laser radiation by the molecule in the gaseous atmosphere. What has just been stated does not mean that the window necessarily has a thickness of 1 mm, it simply being a question of defining an intrinsic transmittance value of the material, in this case for a material thickness of 1 mm. Specifically, the transmittance decreases with thickness and an intrinsic value may be given for a given thickness. The window may for example have a thickness between 0.5 and 20 mm. The smaller the thickness, the more fragile the window. The greater the thickness, the lower the transmittance. For a glass furnace whose internal atmosphere is at a pressure close to atmospheric pressure, a window thickness in the range from 2 to 5 mm (limits inclusive) is generally suitable. In general, the device according to the invention comprises two windows made of a solid material having, for a thickness of 1 mm, a transmittance of greater than 50% and preferably greater than 80% at the wavelength of the laser radiation. The laser beam passes through the first window before passing through the hot atmosphere. The laser beam after having passed through the hot atmosphere passes through the second window. The first window is therefore that through which the laser beam is emitted and the second window is that through which the laser beam is received. In general, these two windows are chosen to be made of the same material.

Advantageously, the laser beam is sufficiently wide for the emerging signal not to be disturbed by the occasional presence of particles along its path. Thus, it is preferable for the cross section of the window orthogonal to the laser beam to have an area of at least 10 cm² and even at least 15 cm². The area of the window is sufficient to let the entire laser beam pass therethrough. Above all, in respect of the window positioned for receiving the laser beam after it has passed through the hot atmosphere, said window preferably has an area at least 30%, and even at least 50%, greater than the area of the cross section of the laser beam. This is because the hot atmosphere of the furnace may slightly deflect the direction of the laser beam depending on any fluctuation of its composition, its temperature and particles lying along its path. Thus, the larger the receiving window, the greater the chance of collecting the entire laser beam. For example, a window area of between 25 and 100 cm² is generally necessary. The wavelength of the laser beam depends on the nature of the molecules the concentration of which it is desired to determine. The table below gives the wavelengths of the laser beam to be used for the desired molecules.

| Molecule | Wavelength of an absorption line between 4 and 8 µm | Material of the window | | | |
| --- | --- | --- | --- | --- | --- |
| | | $CaF_2$ | Sapphire | ZnSe | Fused silica |
| CO | 4.86 µm | 94% | 70% | 62% | 0% |
| NO | 5.26 µm | 95% | 52% | 62% | 0% |
| $NO_2$ | 6.13 µm | 92% | <10% | 62% | 0% |

The window may in particular be made of calcium fluoride ($CaF_2$), sapphire ($Al_2O_3$) or zinc selenide (ZnSe). In the context of the invention, the three aforementioned compounds are advantageously single-crystal compounds. In the latter case, it is preferable for the laser beam to pass through the single crystal orthogonally to the <111> crystal plane in the case of $CaF_2$ and ZnSe and orthogonally to the <0001> crystal plane (along the c-axis) in the case of sapphire.

The window is placed facing an orifice (that is to say along the axis thereof) in a wall of the chamber containing the hot atmosphere to be analyzed. Thus, the emitted laser beam passes through the window and then the orifice in the wall. The orifice in the wall may for example be an orifice provided for cleaning the chamber or may be an orifice provided especially for the measurement.

The window is preferably protected from the gaseous atmosphere by a stream of a gas (for example, air or nitrogen) which is inert with respect to the material of the window and injected between the window and the hot atmosphere. This injection of inert gas prevents the window from being covered with dust coming from inside the chamber and makes it possible for it to be used for a long period without being cleaned.

The window may be incorporated into an insert, said insert being fixed to the wall (at the orifice in the wall), preferably in a sealed manner, so as to prevent the hot atmosphere of the chamber escaping therefrom via the orifice opposite which it is placed. This seal may in particular be obtained especially using a refractory cement bonding the insert to the chamber. However, if the atmosphere in the chamber is substantially at atmospheric pressure, a perfect seal is not necessarily required. Thus the invention also relates to a chamber provided with the device according to the invention, the device being mounted in an at least partly sealed, or even completely sealed, manner in the chamber.

In particular, the window may be fixed in a metal part of the insert. This metal part comprises an orifice through which the laser beam passes. This orifice in the metal part therefore passes right through the metal part. The insert may comprise a tubular part designed to be housed in the thickness of the wall of the chamber. The hollow region of the tubular part (the interior of the tube of the tubular part) constitutes an orifice through which the laser beam passes. This tubular part may in particular be connected to another part comprising the window. The join between these two parts may be achieved using a flange. The tubular part of the insert will be subjected to a temperature close to that within the furnace and therefore must be made of a material resistant to this temperature and to thermal shocks. Advantageously, this material is more refractory than the metal from which the metal part is made, which may be a standard steel. It may be a refractory ceramic (especially mullite) or a refractory concrete or a refractory metal. The insert may include an inlet for gas which is inert with respect to the material of the window, thus protecting the window from the hot atmosphere of the chamber when being used. Thus, a stream of this gas arrives between the window (that face of the window turned toward the inside of the chamber) and the hot atmosphere to be analyzed. This gas, with a low flow rate (for example 0.1 to 50 Nm³/h), may then be directed toward the hot atmosphere and mixed therewith without substantially modifying the gaseous composition inside the chamber. Thus, the window may be incorporated into a metal part of an insert, said metal part comprising an orifice, through which the laser radiation passes, and optionally a cooling water box. The orifice of the metal part is thus obstructed by the window, through which the laser beam can pass. The laser beam can therefore pass right through the insert, encountering as solid material only the window. The inlet of inert gas for protecting the window may be located between the cooling water box and the window. It is also possible to do the reverse, that is to say to place the cooling water box between the inert gas inlet and the window. Thus, the insert may comprise a ceramic part fastened to the metal part, said ceramic part being tubular and allowing the laser radiation to pass along the axis thereof, the axis of the tubular part passing through the orifice of the metal part, and the insert being oriented so that the ceramic part is directed towards the gaseous atmosphere. Thus, the invention also relates to an insert comprising a window made of calcium fluoride or sapphire or zinc selenide, a metal part having an orifice and a tubular part made of a material more refractory than the metal part, the tubular part being fastened to the metal part, the window being incorporated into the metal part, obstructing its orifice, the axis of the tubular part passing through the orifice of the metal part and through the window, the metal part possibly including a water box and the metal part possibly including a gas inlet opening into the orifice of the metal part between the window and the tubular part.

The laser beam may be passed through the laboratory volume of a furnace, said laser radiation then passing from a first lateral wall (sidewall) to a second lateral wall facing the first wall. The laser beam may also be made to pass through the entire atmosphere of the furnace between an upstream wall and a downstream wall. However, depending on the type of furnace, the required path of the laser beam may be slightly too long, so that the emerging beam is slightly too attenuated thereby. Specifically, it is preferable for the distance traveled by the laser through the hot atmosphere to lie within the range from 1 to 3 meters (limits inclusive). This may be the distance between two windows according to the invention—the window through which the laser beam is emitted and the window through which the laser beam is received—the two windows flanking the gaseous atmosphere to be analyzed. It may therefore be of interest to place the laser beam at a position where the flue gas is at least partly collected, such as a stack or a burner duct, that is to say the duct forming the link between a regenerator and a furnace, said duct (also called a port) serving alternately as air intake duct for a burner and as flue gas discharge duct for taking the flue gas to the regenerator. In this case, of course, the laser measurement according to the invention is carried out only when the duct serves to recover the flue gas (and not when the duct serves for the intake of air as oxidant for the burner). The laser device according to the invention may also be placed in the flue gas duct (also called the fume duct) between a furnace and a recuperator.

The invention also relates to a method of measuring the concentration of a molecule in a gaseous atmosphere at a temperature above 1200° C., but generally below 1700° C., by the device according to the invention. This molecule may in particular be a CO or NO or $NO_2$ molecule. Several molecules may be analyzed simultaneously. To do so, it is general practice to use several laser sources, each having an absorption line of a molecule to be analyzed, the various laser beams then being made to pass through the hot atmosphere to be analyzed. The various laser beams may be combined into a single beam before passing through the hot atmosphere.

The invention also relates to a method of heating glass in a glass furnace equipped with burners, the combustion flue gas of which is analyzed by the measurement method according to the invention.

FIG. 1 shows a furnace 1 equipped with the device according to the invention. A laser emitter 2, emitting in the 3 to 24 µm wavelength range, emits the laser radiation 3 through a window 4 fixed to an insert 5, said insert 5 passing through the sidewall 6 of the furnace 1. The laser radiation 3 passes through the hot atmosphere 7 of the furnace and emerges from this atmosphere via a window 8 placed in an insert 9 passing through the sidewall 10 of the furnace, facing the sidewall 6. The exiting laser beam is then used by an analyzer 11 to determine the concentration of a given gas in the atmosphere 7 of the furnace from the amount of absorption of the laser radiation. The laser radiation is directed and sent from the emitter to the analyzer by a set of mirrors 12.

Figure 2:
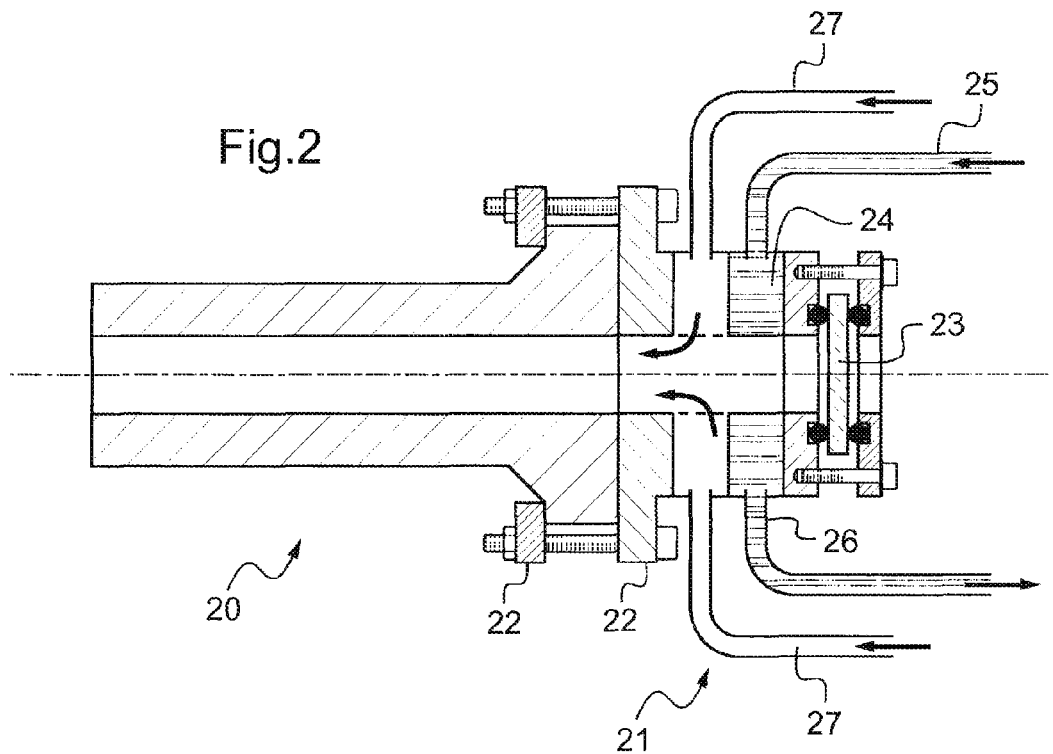

FIG. 2 shows an optical insert according to the invention. It comprises a tubular part 20 made of refractory cement (Licofest MW95C or Licofest H195C) and a metal part 21. These two parts are held fastened together by a flange system 22. The refractory cement part 20 is intended to be inserted into the thickness of the furnace wall. The hollow region of this tubular part (close to the axis) serves for the passage of the laser beam. The metal part 21 serves for holding and cooling the window 23, which may for example be made of a cylindrical single crystal of calcium fluoride ($CaF_2$) with a diameter of 50 mm and a thickness of 3 mm. This metal part includes an orifice (close to the axis) through which the laser beam passes. The orifice of the metal part is obstructed by the window 23, through which the laser beam passes. The window 23 is protected from the hot gases coming from the furnace by a water box 24 and by an air cooling system. The water box is of the annular type, that is to say it goes around the orifice of the metal part without obstructing the center close to the axis of the insert. The water box is supplied with water via a pipe 25, the water emerging via the pipe 26. The air is injected via pipes 27. The flow rate of the air injected in front of the window 23 is for example about 5 $Nm^3/h$. The injected air then passes into the hot atmosphere of the furnace. This flow of air prevents dust coming from the furnace accumulating in the insert. The amount of air coming from the insert and injected into the furnace is negligible compared with the volume of the internal atmosphere of the furnace. The air inlet opens into the orifice of the metal part and is located between the window and the tubular part. In FIG. 2, the inflow of air for protecting the window is placed between the gaseous atmosphere and the water box. It is also possible to do the reverse, that is to say to place the inflow of protective air as close as possible to the window 23 and the water box between the air inlet and the gaseous atmosphere. The insert in FIG. 2 may serve either for emitting the laser beam or for receiving it.

Figure 3:
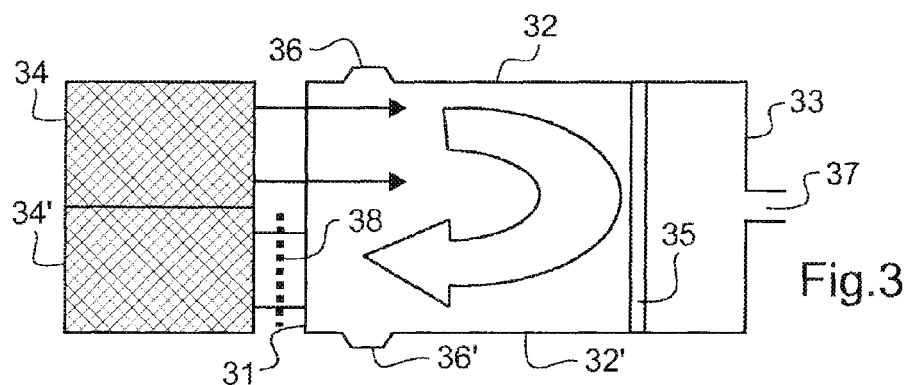
Figure 4:
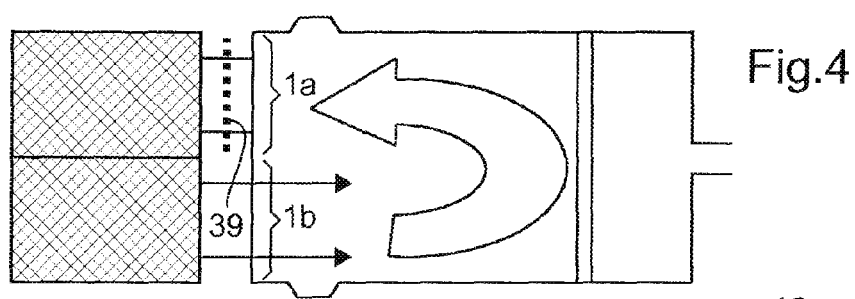

FIG. 3 shows a horseshoe-fired furnace, seen from above, which can be used in the context of the present invention. This furnace comprises an upstream face 31, two lateral faces 32 and 32' and a downstream face 33. It is provided with two identical juxtaposed regenerators 34 and 34', both placed behind the upstream face. Each regenerator is placed behind one half of the upstream face. Feed ports 36 and 36' are provided in the sidewalls 32 and 32' for introducing the batch materials. These feed ports are placed in the first upstream third of the sidewalls. A submerged dam 35 in the melt is provided in the downstream half of the furnace. In the case shown in FIG. 3, the flame is emitted from the half 1a of the upstream face. It forms a horseshoe in the atmosphere of the furnace, returning to the other half 1b of the upstream face. The flue gas then passes through the regenerator 34' placed behind the half 1b of the upstream face. The laser beam 38 of a device according to the invention passes through the duct between the furnace and the regenerator 34' and serves for analyzing the combustion gases. When the refractory bricks in the regenerator 34' are hot enough, the operation of the furnace is reversed, as shown in FIG. 4. In this case, the flame is output from the half 1b of the upstream face and the heat of the flue gas is recovered in the other regenerator 34. Another device according to the invention, generating the laser beam 39 and placed so as to pass through the duct between the furnace and the regenerator 34' is then used. The oxidant for the flame is air reheated on passing through the regenerator 34'. The glass flows through the port 37 provided in the downstream face 33 of the furnace. The fuel injectors are not shown.

Figure 5:
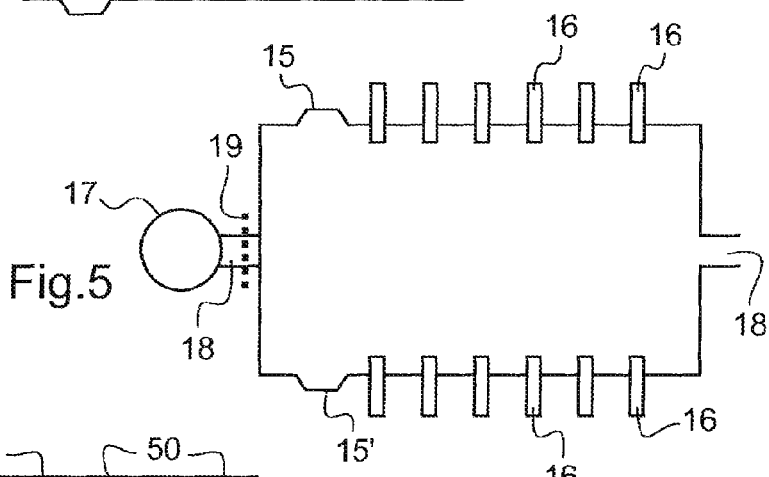

FIG. 5 shows a cross-fired furnace seen from above. The batch materials are introduced via feed ports 15 and 15' located upstream in the sidewalls. Many transverse burners 16 are fitted in the sidewalls. The flue gas is collected via the duct 18 and sent to the recuperator 17. The glass is recovered via the outlet 18. It will be recalled that a recuperator operates on the model of a heat exchanger, the flue gas passing through a channel that reheats the air passing through another channel and supplying the transverse burners. The laser 19 of the device according to the invention passes through the duct 18 for analyzing the combustion gases.

Figure 6:
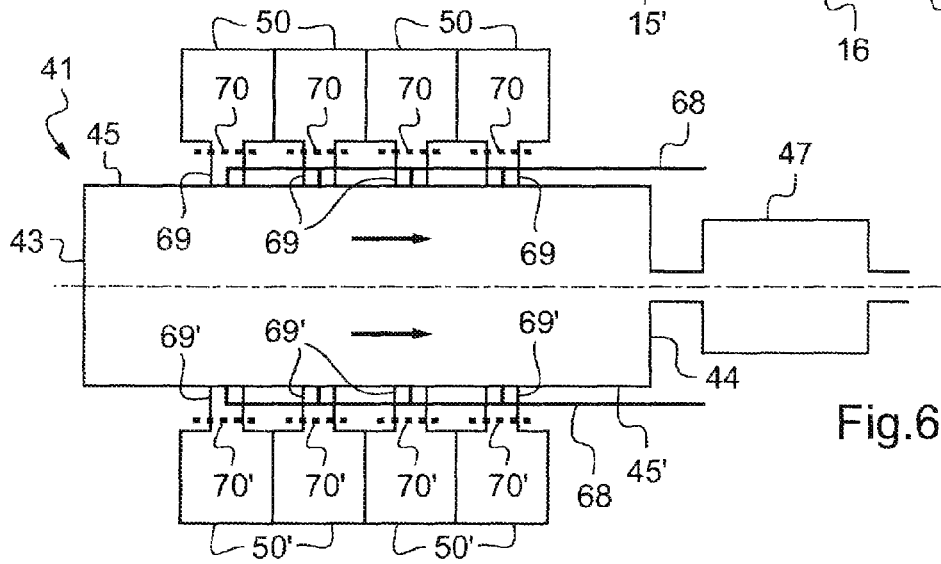

FIG. 6 shows a cross-fired furnace 41 with regenerators. The furnace 41 comprises an upstream wall 43, a downstream wall 44 and two sidewalls 45 and 45'. The batch materials are introduced right at the upstream wall 43 via a standard device (not shown). The molten batch materials flow from the upstream end to the downstream end, as indicated by the arrows. The glass passes through a conditioner 47 for the purpose of thermally conditioning a glass before running into the conversion unit (not shown) and possibly to a float glass installation for producing flat glass. The furnace 41 is equipped through its two sidewalls with two rows of four overhead burners operating one after the other. Each overhead burner comprises at least one fuel injector, supplied with gas via the lines 68 and 68', and a hot air intake 69 and 69'. It may be seen that the first two burners of each sidewall are in the first, upstream third of the furnace (the boundary of this first third is indicated by a transverse dotted line 48). The openings 69 and 69' act alternately as hot air inlet and as flue gas collector. They are each connected to a regenerator 50, 50'. When the injectors in the wall 45 are operating, those in the wall 45' are not operating. The flue gas passes through the ducts 69' in the sidewall 45' facing them and the heat is recovered in the regenerators 50. After a few tens of minutes, the operation of the furnace is reversed, that is to say the operation of the burners in the wall 45 is stopped (by stopping the fuel gas through the line 68 and stopping the air through the duct 69) and the overhead burners in the wall 45' are turned on by supplying the injectors thereof with gas via the line 68' and supplying the line 69' with hot air. The air is hot because it is reheated by the regenerators 50. After a few tens of minutes, the operation of the furnace is again reversed, and so on (repetition of the reversal cycle). Over the time that the regenerators 50 are receiving the flue gas emitted by the burners located in the wall 45', the combustion gases may be analyzed by the series of devices 70 according to the invention, the laser beams of which pass through the ducts 69. A device according to the invention may be placed in each duct 69. Over the time that the regenerators 50' are receiving the flue gas emitted by the burners located in the wall 45, the combustion gases may be analyzed by the series of devices 70' according to the invention, the laser beams of which pass through the ducts 69'. A device according to the invention may be placed at each duct 69'. This system thus provides an individual gas analysis for each burner, enabling it to be individually adjusted.

Trials under real conditions carried out on a glass furnace have shown that the window does not break when fitted into the insert and maintains its transparency well. The window was mounted in an insert as shown in FIG. 2 with a water box and with cool air flowing over the window. The temperature of the window, measured during a trial, was 60° C. for a furnace temperature of 1500° C.

The invention claimed is:

1. A device for measuring the concentration of a molecule in a gaseous atmosphere at a temperature above 1200° C. in a chamber, said molecule having an absorption line at a wavelength between 4 and 8 µm, said device comprising:
    an emitter that emits laser radiation with a wavelength corresponding to that of the absorption line of said molecule, said emitter emitting the laser radiation through a first window and then through said gaseous atmosphere, said first window comprising a solid material, the solid material having a transmittance greater than 50% measured on one mm thick of the material at the wavelength of the laser radiation, the laser radiation being analyzed after passing through said atmosphere by an analyzer that determines the absorption of the laser radiation by the molecule in the gaseous atmosphere,
    wherein the window is placed on or in a wall of the chamber, where appropriate via an insert, to prevent hot atmosphere of the chamber from escaping therefrom.

2. The device of claim 1, wherein the transmittance of the material, measured on one mm thick of the material, is greater than 80% at the wavelength of the laser radiation.

3. The device of claim 1, wherein the first window is protected from the gaseous atmosphere by a stream of a gas which is inert with respect to the material of the first window and is injected between the first window and the hot atmosphere.

4. The device of claim 1, wherein the first window is incorporated into an insert placed on or in a wall of the chamber.

5. The device of claim 4, wherein the first window is incorporated in a metal part of the insert, said metal part comprising an orifice for passage of the laser radiation and optionally a cooling water box.

6. The device of claim 5, wherein the insert comprises a ceramic part fastened to the metal part, wherein said ceramic part is tubular and allows the laser radiation to pass along its axis, the axis of the tubular part passing through the orifice of the metal part, and wherein the insert is oriented such that the ceramic part is directed toward the gaseous atmosphere.

7. The device of claim 1, wherein the first window comprises calcium fluoride, sapphire, or zinc selenide.

8. The device of claim 7, wherein the first window is a single-crystal window.

9. The device of claim 1, wherein the first window has a thickness in a range from 0.5 to 20 mm.

10. The device of claim 1, wherein the laser radiation has a cross section of area greater than 10 cm$^2$.

11. The device of claim 1, wherein the laser beam passes through a second window after said atmosphere, said second window having an area more than 30%, greater than the area of the cross section of the laser beam.

12. The device of claim 1, wherein the laser radiation passes through from 1 to 3 m of the gaseous atmosphere.

13. A chamber, equipped with the device of claim 1.

14. The chamber of claim 13, wherein the device is sealingly mounted in the chamber.

15. The chamber of claim 13, which is a flue gas duct connecting a glass furnace to a regenerator or a recuperator.

16. The chamber of claim 13, which is a glass furnace or a flue gas duct connected to a glass furnace.

17. A method of measuring the concentration of a molecule in a gaseous atmosphere at a temperature above 1200° C. in a chamber with the device of claim 1, said molecule having an absorption line at a wavelength between 4 and 8 μm, the method comprising:

emitting laser radiation of wavelength corresponding to that of the absorption line from the emitter of the device through the first window and then through said gaseous atmosphere; and analyzing the laser radiation after having passed through said atmosphere with an analyzer that determines the absorption of the laser radiation by the molecule in the gaseous atmosphere.

18. The method of claim 17, wherein the gaseous atmosphere is at a temperature below 1700° C.

19. The method of claim 17, wherein the molecule is CO, NO, or $NO_2$.

20. A method of heating glass in a glass furnace equipped with burners, the method comprising:

analyzing a combustion flue gas with the method of claim 17.

21. An insert comprising:

a window comprising calcium fluoride, sapphire, or zinc selenide;

a metal part having an orifice; and a tubular part comprising a material more refractory than the metal part, wherein the tubular part is fastened to the metal part, and wherein the window is incorporated into the metal part, obstructing its orifice, the axis of the tubular part passing through the orifice of the metal part and through the window, the metal part optionally including a water box and the metal part optionally including a gas inlet opening into the orifice of the metal part between the window and the tubular part.

\* \* \* \* \*